United States Patent [19]

Clotfelter et al.

[11] 3,938,037
[45] Feb. 10, 1976

[54] DEVICE FOR MEASURING THE FERRITE CONTENT IN AN AUSTENITIC STAINLESS STEEL WELD MATERIAL

[75] Inventors: Wayman N. Clotfelter; Benjamin F. Bankston, both of Huntsville, Ala.

[73] Assignee: The United States of America as represented by the United States National Aeronautics and Space Administration, Washington, D.C.

[22] Filed: Oct. 29, 1974

[21] Appl. No.: 518,546

[52] U.S. Cl. .............................. 324/34 R
[51] Int. Cl.² ................................. G01R 33/12
[58] Field of Search .......... 324/34 R, 34 PE, 34 TK

[56] References Cited
UNITED STATES PATENTS

| | | | |
|---|---|---|---|
| 3,013,204 | 12/1961 | Ford, Jr. et al. | 324/34 R |
| 3,244,971 | 4/1966 | Thompson | 324/34 TK |

OTHER PUBLICATIONS

Entin, S. D.; Mag. Method of Quantitative Determination of Ferrite In Weld National; Weld Proc.; Vol. 19; No. 2 (Feb. 1972) pp. 21–26.

*Primary Examiner*—Robert J. Corcoran
*Attorney, Agent, or Firm*—Wayland H. Riggins; L. D. Wofford, Jr.; John R. Manning

[57] ABSTRACT

A device is provided for measuring the ferrite content of austenitic stainless steel weld material. The device includes a base plate for rotatably mounting a mechanical vernier member thereupon; the mechanical vernier member supports a cantilever beam in a manner to provide vertical positioning of the beam. Suspended from the free end of the beam is a permanent magnet below which is positioned the specimen of austenitic weld material which is to be tested. Strain gauges are provided on the top surface of the beam for measuring the magnetic force between the magnet and weld material by measuring the amount of downward deflection of the beam. The measurement is then converted into a reading which indicates the percentage of ferrite of the weld material in the joint.

5 Claims, 2 Drawing Figures

DEVICE FOR MEASURING THE FERRITE CONTENT IN AN AUSTENITIC STAINLESS STEEL WELD MATERIAL

Origin of the Invention

The invention described herein was made by employees of the United States Government and may be manufactured and used by or for the Government for governmental purposes without the payment of any royalties thereon or therefor.

BACKGROUND OF THE INVENTION

This invention relates to a device for measuring the ferrite content in a weld deposit of an austenitic stainless steel weld material. A small but controlled amount of ferrite is effective in preventing cracking of austenitic stainless steel weld deposits and therefore it is important to know, as accurately as possible, the exact amount of ferrite present in the weld joint deposit. An incorrect amount of ferrite in the weld deposit leads to cracking and deterioration of the welded joint. Types of ferrite-containing austenitic weld metals which take advantage of the effect of ferrite include among others the 308, 308L, 309, 347, and 318 electrode or rod types. In cooling from the molten state austenitic stainless weld metal of normal carbon content solidifies first as a mixture of ferrite and austenite; most of the ferrite subsequently transforms to austenite as the deposit cools. The two factors which have the greatest affect on the ferrite content of the weld deposit are the chemistry of the weld electrode or rod and the welding technique itself.

Heretofore, the amount of ferrite in stainless steel weld deposits has been determined in any of several ways. Metallographic examination of the deposit can provide an approximate indication of the ferrite content in terms of area distribution. However, such a method is cumbersome and requires considerable care to be sure that the sections examined give a true picture of the volumetric ferrite distribution. Various diagram methods have been used for calculating the amount of ferrite in weld deposits based on chemical analysis by graphically combining effects of the austenitizers nickel, carbon, and manganese, and the ferritizers chromium, molybdenum, silicon, and columbium. However, the accuracy of such calculations depends on how accurately the chemistry of the weld deposit is known. Some of the more well known diagram methods include the Schaeffler and the DeLong diagrams.

Prior art devices have been developed which use a magnet suspended from a beam and associated strain gauges for measuring the thickness of a material, such as U.S. Pat. No. 3,244,971. However, such devices are rather complicated as they are used for measuring flexing in two directions and would not provide for the precision required for measuring very small amounts of ferrite. Other prior art devices such as shown in U.S. Pat. No. 3,745,449 use electronic circuitry for measuring uniform wall thickness in the welded joints of tubular pipe by detecting magnetic flux variations in the weld line, but such a device would not be suitable for accurately measuring small amounts of ferrite.

SUMMARY OF THE INVENTION

It has been found, in accordance with the present invention, that an accurate instrument device can be constructed for meaasuring the ferrite content in austenitic stainless steel. The device includes a base plate having mounted thereon an adjustable mechanical vernier member for supporting a cantilever beam and for finely adjusting the position of the beam in a vertical direction. Suspended from the free end of the beam is a small permanent magnet. Strain gauge means are mounted on the beam for measuring the deflection thereof. The strain gauge means are connected in a suitable Wheatstone bridge circuit for representing the strain gauge measurement as an electrical signal. An appropriate indicating meter is connected to the output of the bridge circuit for converting the electrical signal generated thereby into a signal representative of the percent of ferrite present in a tested specimen of austenitic stainless steel weld material. As the specimen is placed below the magnet, the magnet is allowed to "grab" the specimen and the resulting deflection of the cantilever beam is converted into a signal representing the ferrite content of the specimen as described above.

Accordingly, an important object of the present invention is to provide a device for accurately measuring the ferrite content in austenitic stainless steel weld material.

Another important object of the present invention is to provide a device which is rather simple and compact in operation and construction and can be effectively used either in the laboratory or in the field for accurately measuring the ferrite content in austenitic stainless steel material.

Still another important object of the present invention is to provide a device for determining the correct amount of ferrite in an austenitic stainless steel weld material so as to prevent cracking and deterioration of the weld joint.

BRIEF DESCRIPTION OF THE DRAWING

The construction designed to carry out the invention will be hereinafter described, together with other features thereof.

The invention will be more readily understood from a reading of the following specification and by reference to the accompanying drawing forming a part thereof, wherein an example of the invention is shown and wherein.

DESCRIPTION OF THE PREFERRED EMBODIMENT

Figure 1:
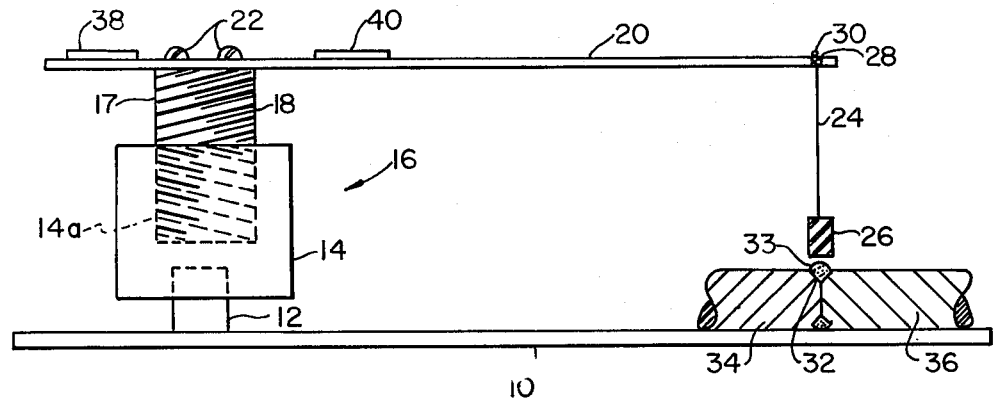
FIG. 1 is a schematic illustration of a device for measuring the ferrite content of austenitic stainless steel weld material constructed in accordance with the present invention.

Referring now to FIG. 1, there is illustrated a ferrite measuring device in accordance with the present invention which includes a base plate 10 having a spindle 12 fixed thereon. Rotatably mounted on spindle 12 is a base portion 14 of a mechanical vernier designated broadly as 16. A threaded member 18 of the mechanical vernier 16 is received in a threaded bore 14a of base 14 for providing a fine screw adjustment for raising and lowering the member 18. The threaded member 18 may include a vernier scale at 17 attached thereto, the detailed scale being omitted for purposes of clarity. Attached to the top of threaded member 18 is a cantilever beam 20 which is fixed to member 18 by using screws 22 or any other suitable attaching means. Suspended from the free end of the beam 20 is a flexible braided member 24 which has a small permanent magnet 26 attached to the end thereof. Braided member 24 is attached to the end of beam 20 by inserting the end of member 24 through a small hole 28 and then forming a knot 30 in the end of braided member 24, or member 24 may be attached in any other suitable manner. Positioned below magnet 26 is a welded joint 32 containing weld material 33 which is formed, as for example, by the welding together of the two rod or pipe sections 34 and 36. Mounted on the top surface of beam 20 is a reference strain gauge 38 and a measuring strain gauge 40 of the SR-4 wire type.

Figure 2:
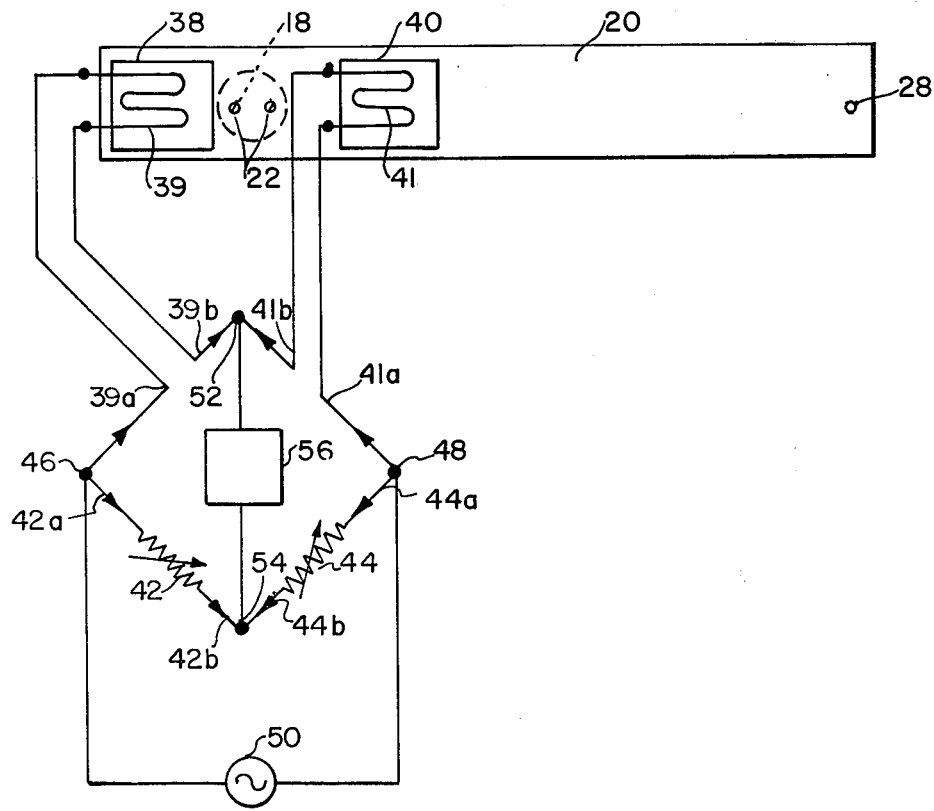
FIG. 2 is a schematic illustration showing a top view of the device of FIG. 1 and further showing a schematic circuit diagram constructed in accordance with the present invention.

Referring now to FIG. 2, a top view of the cantilever beam 20 is shown with the stain gauges 38 and 40 mounted thereon having resistive elements 39 and 41, respectively. The wiring of resistive elements 39 and 41 is so arranged to form a Wheatstone bridge circuit along with conventional resistors 42 and 44, as shown in FIG. 2. The input conductors 39a and 42a leading to resistive element 39 and resistor 42, respectively, are connected to the input terminal 46 and input conductors 41a and 44a leading to resistive element 41 and resistor 44, respectively, are connected to the input terminal 48. Input terminals 46 and 48 are connected to a suitable current source 50. Output conductors 39b and 41b leading from resistive elements 39 and 41, respectively, are connected to an output terminal 52 and the output conductors 42b and 44b leading from resistors 42 and 44, respectively, are connected to output terminal 54. Output terminals 52 and 54 are connected to indicating meter 56 which indicates the amount of ferrite measured in the weld joint 32 in a manner to be more fully described later.

Measuring strain gauge 40 is located on the top of beam 20 so as to cause the resistive element 41 to stretch as beam 20 is deflected downwardly. Reference strain gauge 38 compensates for environmental temperature changes, and is not placed on the beam 20 for detecting the downward flexing of the beam. One or both of the resistors 42 and 44 in the remaining branches of the bridge may be adjustable so as to provide for adjusting the current in the bridge circuit to zero prior to testing a specimen. The indicating meter 56 may include a conventional galvanometer which has a scale marked off in arbitrary divisions rather than in amperes or volts. The divisions may include percentages of ferrite content, for example. Standard specimens of weld metal having known percentages of ferrite content can be placed under the magnet 26 and measured in order to calibrate the divisions of the meter 56.

In use, the bridge circuit is first balanced by adjusting the current to zero, then the weld joint 33 is placed under the magnet 26 and the base member 14 of mechanical vernier 16 is rotated to provide for a fine adjustment in raising and lowering the beam 20 and thus magnet 26. As the magnet is gradually lowered, it grabs the weld material 33 in the joint 32. Then, the force required to pull the magnet away is measured with the strain gauge 40 instrumentation. More specifically, as the beam 20 and magnet 26 are gradually raised, the strain gauge 40 measures the strain caused by the downward flexing or deflection of beam 20 until the force of attraction between magnet 26 and the weld material 33 is overcome. When the beam is flexing, the strain on gauge 40 causes the resistive element 41 to stretch causing its resistance to the current passing therethrough to change. Stretching of the resistive element 41 will result in an increase in the resistance. With the resistive members 39, 41, and resistors 42 and 44 wired together to form a Wheatstone bridge circuit, the change in resistance of the strain gauge will have the effect of changing the balance of the bridge circuit with the degree of unbalance being registered on the meter 56 as representing the percentage of ferrite present in the weld material specimen 33.

In the event that very weak signals of unbalance are produced in the bridge circuit, as may be necessary in measuring very small concentrations of ferrite, the meter 56 may be readily adapted to include conventional amplifying means to amplify the signal.

A non-contact mode of operation is also possible. This involves placing the device so the magnet is near a specimen, but not near enough to "grab" it. In this mode, the adjustable support is moved only to change the range of the instrument. Of course the system would have to be calibrated for each range position of the support. The ferrite content of a specimen is determined by deflection of the cantilever beam which is proportional to the force of attraction between magnet and specimen. As in the first mode of operation, the deflection is measured with strain gages.

While a preferred embodiment of the invention has been described using specific terms, such description is for illustrative purposes only, and it is to be understood that changes and variations may be made without departing from the spirit or scope of the following claims.

What is claimed is:

1. A device for measuring the ferrite content in an austenitic stainless steel weld material comprising:
   a. a base plate;
   b. a support member;
   c. means mounted adjacent one end of said base plate for adjustably positioning said support member in a vertical direction;
   d. a cantilever beam mounted on said support member;
   e. a permanent magnet suspended from the free end of said cantilever beam;
   f. strain gauge means mounted on said cantilever beam for measuring the amount of deflection of said beam;
   g. instrumentation means connected with said strain gauge means for converting the amount of deflection of said beam into a signal indicating the ferrite content of a specimen of austenitic weld material; whereby said magnet is lowered by adjusting said support member downwardly until said magnet magnetically grabs said specimen of weld material whereupon said magnet is raised by adjusting said support member upwardly until the force of attraction is overcome at which time the deflection of the beam is measured by said strain gauge means to indicate the content of ferrite present in the weld material specimen.

2. The device of claim 1 wherein said strain gauge means includes a measuring strain gauge located on said cantilever beam so as to measure the deflection of said beam and a reference strain gauge located on said beam so as to compensate for environmental temperature variations.

3. The device as set forth in claim 2, wherein said instrumentation means includes:
   a. a Wheatstone bridge circuit having four branches;

b. said measuring strain gauge being connected in one branch of said bridge circuit so as to provide a signal of unbalance representative of said deflection of said beam;

c. said reference strain gauge being connected in a second branch of said bridge circuit;

d. adjustable resistor means connected in the third and fourth branches of said bridge circuit; and e. indicating meter means for representing said signal of unbalance as an indication of said ferrite content of said specimen.

4. In a device for measuring the ferrite content in an austenitic stainless steel weld specimen including a permanent magnet adapted to be disposed in an adhered relationship with a selected specimen for establishing a magnet couple between the specimen and the permanent magnet, the improvement comprising:

means for measuring the intensity of the magnetic force of attraction established between the permanent magnet and a selected specimen adhered to the magnet and proportional to the ferrite content of the specimen including, a. a flexible beam;

b. a base supporting said beam at one end thereof and characterized by means for elevating the beam along a path angularly related to the longitudinal axis thereof;

c. means including a flexible line attached to the magnet and suspended from the end of the beam opposite said one end for positioning said magnet in an adhered relationship with a selected specimen characterized by a ferrite content, whereby flexural motion proportional to the ferrite content of the specimen is imparted to the beam in response to the intensity of the magnetic force of attraction as said beam is elevated; and d. means for measuring the flexural motion imparted to said beam.

5. The improvement of claim 4 wherein said means for measuring the flexural motion imparted to the beam includes a strain gauge mounted on said beam.

* * * * *